(12) United States Patent
Maynard et al.

(10) Patent No.: US 9,566,396 B2
(45) Date of Patent: *Feb. 14, 2017

(54) MEDICAL HAND AND ARM PROTECTION APPARATUS AND METHOD OF PROTECTION

(71) Applicant: Board of Trustees of the University of Arkansas, Little Rock, AR (US)

(72) Inventors: Fereshteh K. Maynard, Conway, AR (US); Jeffery B. Wilkerson, Little Rock, AR (US); Victoria L. Eskew, Benton, AR (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/951,791

(22) Filed: Nov. 25, 2015

(65) Prior Publication Data

US 2016/0074601 A1 Mar. 17, 2016

Related U.S. Application Data

(63) Continuation of application No. 14/146,532, filed on Jan. 2, 2014, now Pat. No. 9,227,026, which is a continuation of application No. 13/007,304, filed on Jan. 14, 2011, now Pat. No. 8,646,457.

(51) Int. Cl.
| | |
|---|---|
| *A61M 5/52* | (2006.01) |
| *A61G 13/10* | (2006.01) |
| *A61G 13/12* | (2006.01) |
| *A61F 5/058* | (2006.01) |

(52) U.S. Cl.
CPC ............ *A61M 5/52* (2013.01); *A61F 5/05866* (2013.01); *A61G 13/10* (2013.01); *A61G 13/124* (2013.01); *A61G 13/1235* (2013.01)

(58) Field of Classification Search
CPC A61M 5/52; A61M 25/02; A61M 2025/0246; A61M 2025/0213; A61B 19/00
See application file for complete search history.

(56) References Cited

U.S. PATENT DOCUMENTS

| | | | | |
|---|---|---|---|---|
| 4,928,712 A | * | 5/1990 | Mele | A61M 5/52 128/877 |
| 5,301,690 A | * | 4/1994 | Lewis | A61B 17/43 128/849 |
| 8,646,457 B2 | * | 2/2014 | Maynard | A61G 13/10 128/877 |
| 2004/0103904 A1 | * | 6/2004 | Auerbach | A61B 19/12 128/856 |
| 2007/0073227 A1 | * | 3/2007 | Hewes | A61F 7/007 604/110 |

* cited by examiner

*Primary Examiner* — Ophelia A Hawthorne
(74) *Attorney, Agent, or Firm* — Richard Blakely Glasgow

(57) ABSTRACT

A medical hand and arm protection apparatus and method of protection including a protective shell which is capable of receiving a patient's hand and arm. A sheet is attached to the protective shell, which is tucked under the patient to anchor the hand and arm protector in place. The protective shell also has one or more perforations that allow the medical professional access to the interior of the surgical arm protector to view the patient's IV sites and other medical equipment attached to the patient's hand or arm.

7 Claims, 6 Drawing Sheets

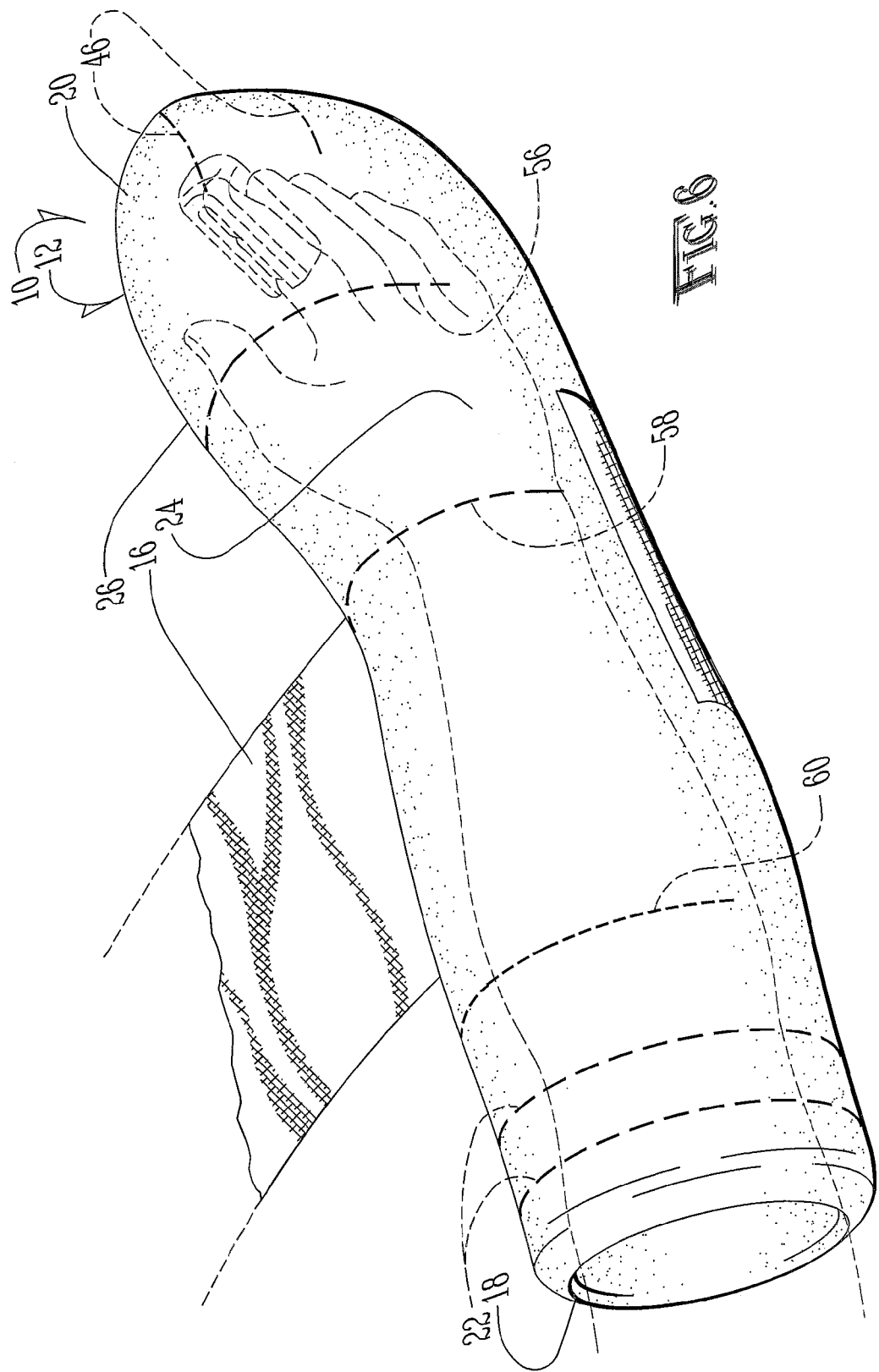

MEDICAL HAND AND ARM PROTECTION APPARATUS AND METHOD OF PROTECTION

CROSS-REFERENCE TO RELATED APPLICATIONS

This application is a continuation application of, and claims the benefit of, U.S. patent application Ser. No. 14/146,532, filed Jan. 2, 2014, now U.S. Pat. No. 9,227,026 B2 and issued on Jan. 5, 2016, which is a continuation application of and claims the benefit of U.S. patent application Ser. No. 13/007,304, filed Jan. 14, 2011, now U.S. Pat. No. 8,646,457 and issued on Feb. 11, 2014, which are incorporated by reference in their entirety.

STATEMENT REGARDING FEDERALLY FUNDED SPONSORED RESEARCH OR DEVELOPMENT

Not applicable

BACKGROUND OF THE INVENTION

1. Field of the Invention

The present invention relates to medical hand and arm protectors, and in particular to medical hand and arm protectors capable of allowing access to intravenous (IV) sites, and other medical equipment connected to the patient's hand and arm during surgery, medical treatment, and/or recovery.

2. Brief Description of the Related Art

During many types of surgeries and medical procedures, including neurosurgery, cardiac surgery, ear, nose, and throat (ENT) surgery, robotic-performed surgeries, pacemaker procedures, I-port procedures, and other local procedures, the arms of the patient must be tucked to their side. Most commonly, the patient's arm is placed on a piece of foam either on the bed or a sled and taped to another piece of foam that is placed on top of the patient's arm. The draw sheet that the patient is laying on is then pulled over the arm and tucked back underneath the patient to secure their arm.

The inventors have observed that this process of tucking the patient's arms commonly requires up to 15 minutes of valuable time in the operating room. In addition, the inventors have recognized the potential for nerve injuries to the patient's arm, burns to the patient's hands, and the lack of easy access to IV sites using the prior art apparatus and method.

Nerve damage can result either because the arm is pulled too tight, the arm is not resting on a sufficiently padded surface, or because the arm is not positioned anatomically correct during the tucking process. Ulcers from decreased blood circulation can also result when the pressure points of the arm or bony prominences are not padded properly. In addition to during surgery and other medical procedures, nerve damage can also occur in patients that are bedridden, especially when the patients are unable to move their arms.

The inventors also recognize the risk for burns to the patient's hands during surgery. If the patient's finger tips are not properly covered during surgery, the fingers may come in contact with a hot surface, including the bed, the sled, or a cautery that is being used during the surgery.

As described above and in U.S. Pat. No. 5,546,963 to Doody, surgical arm protectors are known in the art. However, the prior art arm protectors do not allow adequate access to the patient's IV sites, and other medical instruments connected to the patient's arm or hand during surgery, medical treatment, and/or recovery. Specifically, all patients have at least one IV connected to their hand or arm ranging from the antecubital region of the arm, forearm, wrist, and/or back of the hand. In addition, in some cases, patients require an arterial line which is usually placed in the wrist to draw blood to monitor the patient's blood pressure and blood oxygen level. In order to draw blood from this line, the anesthesiologist must have free access to this line. However, with the prior art apparatus and method of tucking, the anesthesiologist is frequently required to get under the sheet to reposition and re-tuck the arm because the arterial line is extremely sensitive. The pressure from tight tucking causes movement and sometimes loss of the line. In addition, the arterial line and the other IV lines can get caught in the frame of the bed and the other appliances clamped to the bed during surgery if they are not properly stowed and secured. Easy IV site access is even more challenging in robotic surgeries where the patient is placed in a sharp trendelenberg position.

It would therefore be desirable to develop a medical hand and arm protector that is capable of providing support and protection of the arm during surgery, medical treatment, and/or recovery, while also allowing the medical professional access to IV sites and other medical equipment that is connected to the patient's hand and arm.

BRIEF SUMMARY OF THE INVENTION

The present invention is directed to a medical hand and arm protection apparatus comprising (a) a protective shell capable of receiving a patient's arm and having a top section and a bottom section, wherein said top section has at least one perforation along its width, and (b) a sheet attached to said protective shell.

The present invention is also directed to a medical hand and arm protection apparatus comprising (a) a protective shell capable of receiving a patient's arm and comprising at least one perforated panel, said perforated panel comprising two vertical perforations connected by one perpendicular perforation, said perpendicular perforation and said two vertical perforations forming a releasable flap when said perforations are broken, and (b) a sheet attached to said protective shell.

The present invention is also directed to a method for protecting a patient's hand and arm during surgery, medical treatment, and recovery comprising: (a) placing the patient's arm in the protective shell of the surgical hand and arm protection apparatus described above and (b) tucking the sheet of the surgical hand and arm protection apparatus underneath the patient's body.

These and other features, objects and advantages of the present invention will become better understood from consideration of the following detailed description of the preferred embodiments, in conjunction with the drawings as described immediately below.

BRIEF DESCRIPTION OF THE SEVERAL VIEWS OF THE DRAWINGS

FIG. 6 is a perspective view of the first side of the second preferred embodiment of the medical hand and arm protection apparatus.

DETAILED DESCRIPTION OF THE INVENTION

Figure 1:
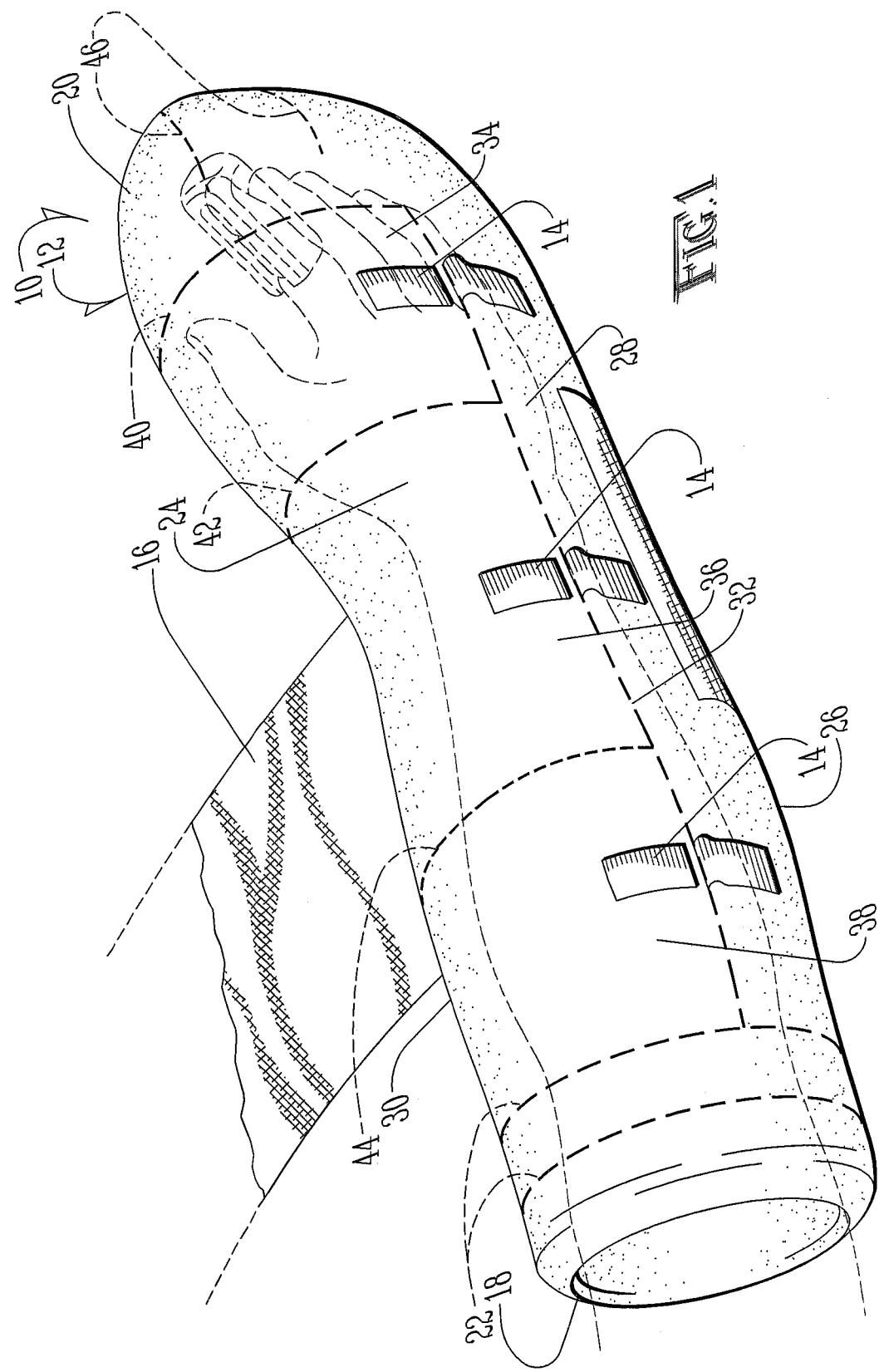
FIG. 1 is a perspective view of the first side of the first preferred embodiment of the medical hand and arm protection apparatus.
Figure 2:
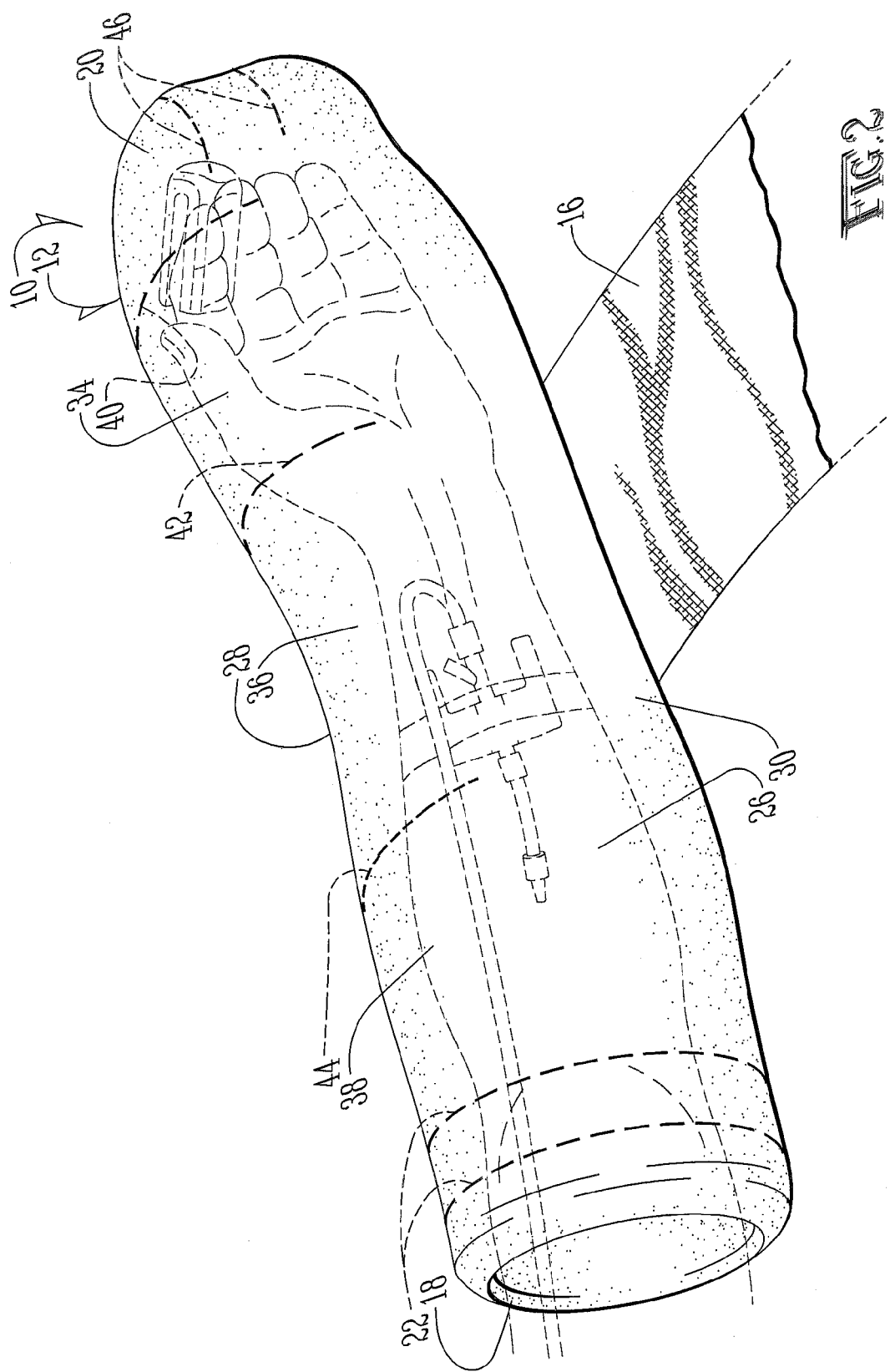
FIG. 2 is a perspective view of the second side of the first preferred embodiment of the medical hand and arm protection apparatus.
Figure 3:
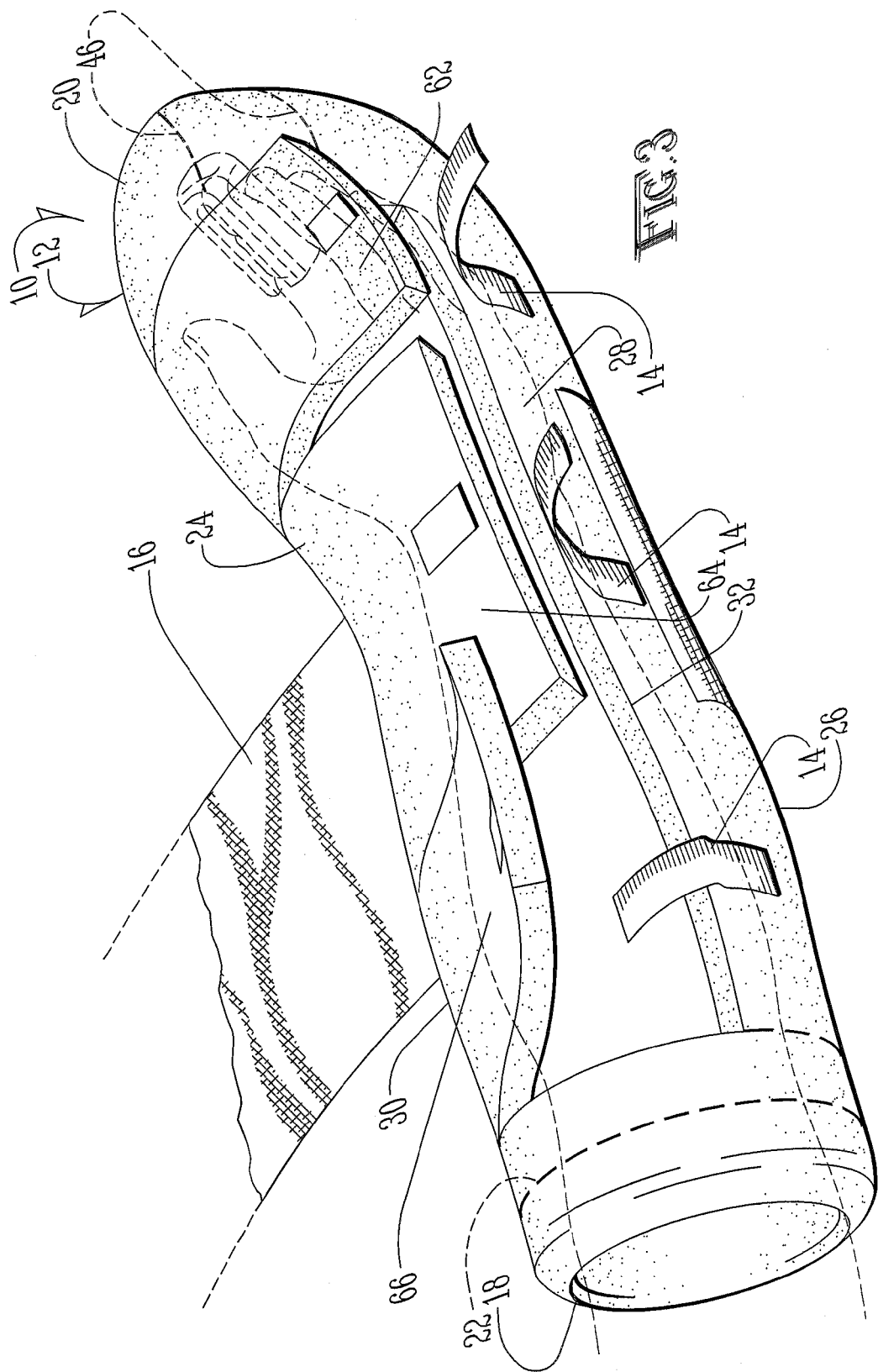
FIG. 3 is a perspective view of the first side of the first preferred embodiment of the medical hand and arm protection apparatus showing the releasable flaps formed when the perforations are broken.
Figure 4:
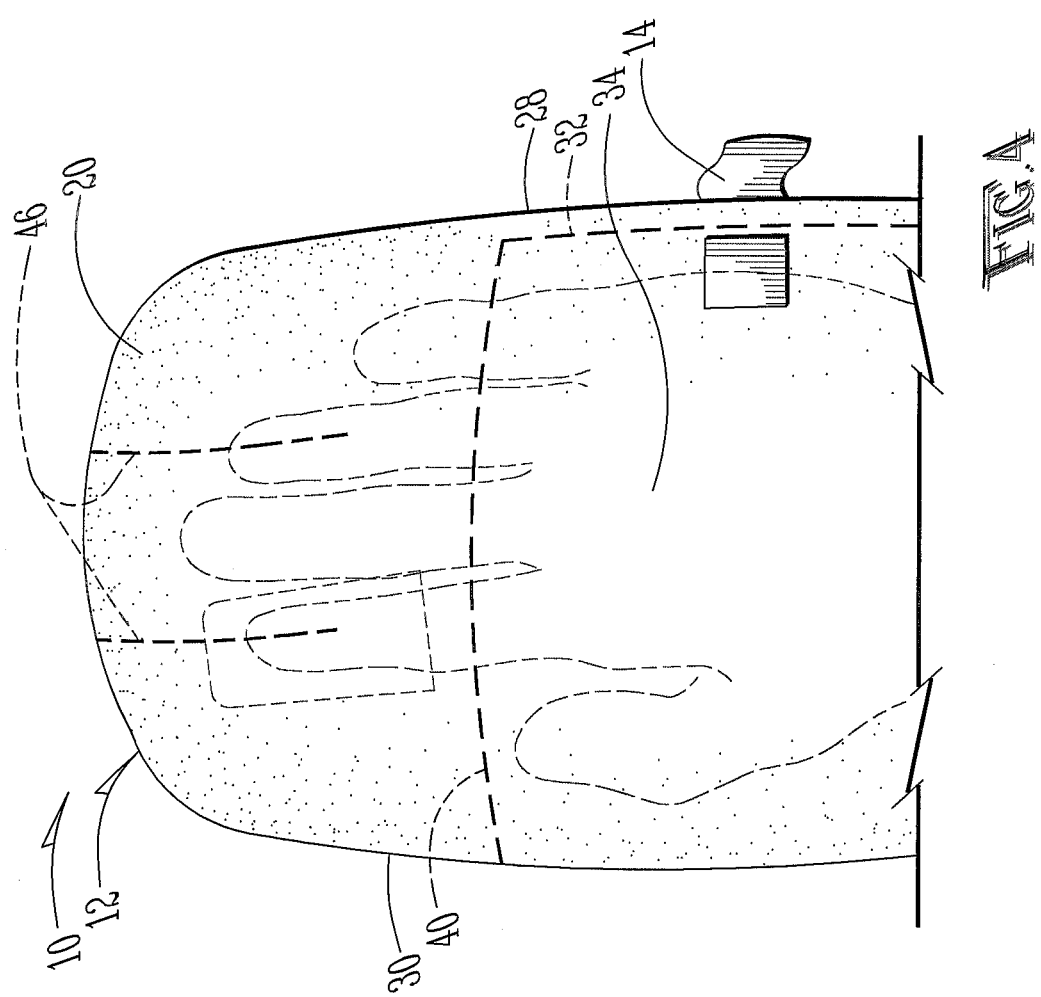
FIG. 4 is a top view of the second end of the first preferred embodiment of the medical hand and arm protection apparatus.

With reference to FIGS. 1-6, the preferred embodiments of the present invention may be described. The medical hand and arm protection apparatus 10 is comprised of a protective shell 12, connecting strap(s) 14, and a sheet 16. The protector 10 is universal for both right and left arms of patients.

In the preferred embodiments, the protective shell 12 has a first end 18 and a second end 20. The shell 12 is open at the first end 18 such that a hand and arm can be slid into the shell 12, and closed at the second end 20 to fully cover and protect the hand and fingers of the patient. The hand and arm can be slid into the shell 12 either flat (i.e. top of hand facing up and palm of hand facing down) or on their side. The protective shell 12 is preferably made of foam or other material that is light in weight, soft, inexpensive, and capable of being manipulated. The shell 12 is preferably cylindrical in shape, but it may be rectangular or other suitable shapes. The shell 12 is preferably 27 inches in length. However, for child patients, the shell is preferably shorter in length. The interior of the protective shell 12 is large enough to fully engage and enclose the patient's hand and arm, and the medical equipment that is attached to the patient's hand or arm, including but not limited to, IV lines, pulse oximeters, and massaging arm wrap devices.

Protective shell 12 is perforated. A perforation is defined as a line of small holes for tearing. Perforation 22 is located at the first end 18 of shell 12 and extends completely around the circumference of the shell 12. Perforation 22 can be broken which allows the shell 12 to be shortened to adapt it to the length of the patient's arm. In the preferred embodiments, the shell 12 has at least one perforation 22 preferably 1.5 inches from the first end of the shell 12. The shell may have an additional perforation 22 which is 1.5 inches from the first perforation. Thus, in the preferred embodiment, the shell is 27 inches in length and, through use of the perforations 22, can be quickly adapted to 25.5 inches or 24 inches in length. The number of perforations 22 and the distance between perforations 22 are variable.

In the first preferred embodiment, the protective shell 12 has a top section 24 and a bottom section 26, and a first side 28 and a second side 30. Along the first side 28 of the protective shell 12 is perforation 32. Perforation 32 extends longitudinally along the entire first side 28 of the shell 12. Perforation 32 preferably runs along the middle of the first side 28 of the shell 12.

The top section 24 of shell 12 is the top cross-section of the shell 12. Conversely, the bottom section 26 of shell 12 is the bottom cross-section of the shell 12. The top section 24 of protective shell 12 has perforated panels 34, 36, 38 which allow the medical professional access to the hand and arm. In the preferred embodiment, perforation 32 is laterally intersected by three perforations 40, 42, 44, which create perforated panels 34, 36, 38. Perforations 40, 42, 44 extend laterally along the entire top section 24 of the shell 12. The first perforated panel 34 is in the hand region of the surgical arm protector 10. The second perforated panel 36 is in the wrist region and the third perforated panel 38 is in the elbow region. The elbow region includes the brachial, antecubital, and forearm sections of the arm. Thus, for example, if the medical professional needs to check the IV site located in the patient's wrist, perforated panel 36 is utilized by breaking the perforations of longitudinally extending perforation 32 and laterally extending perforations 42, 44. Breaking the perforations of perforated panels 34, 36, 38 forms releasable flaps 62, 64, 66.

Figure 5:
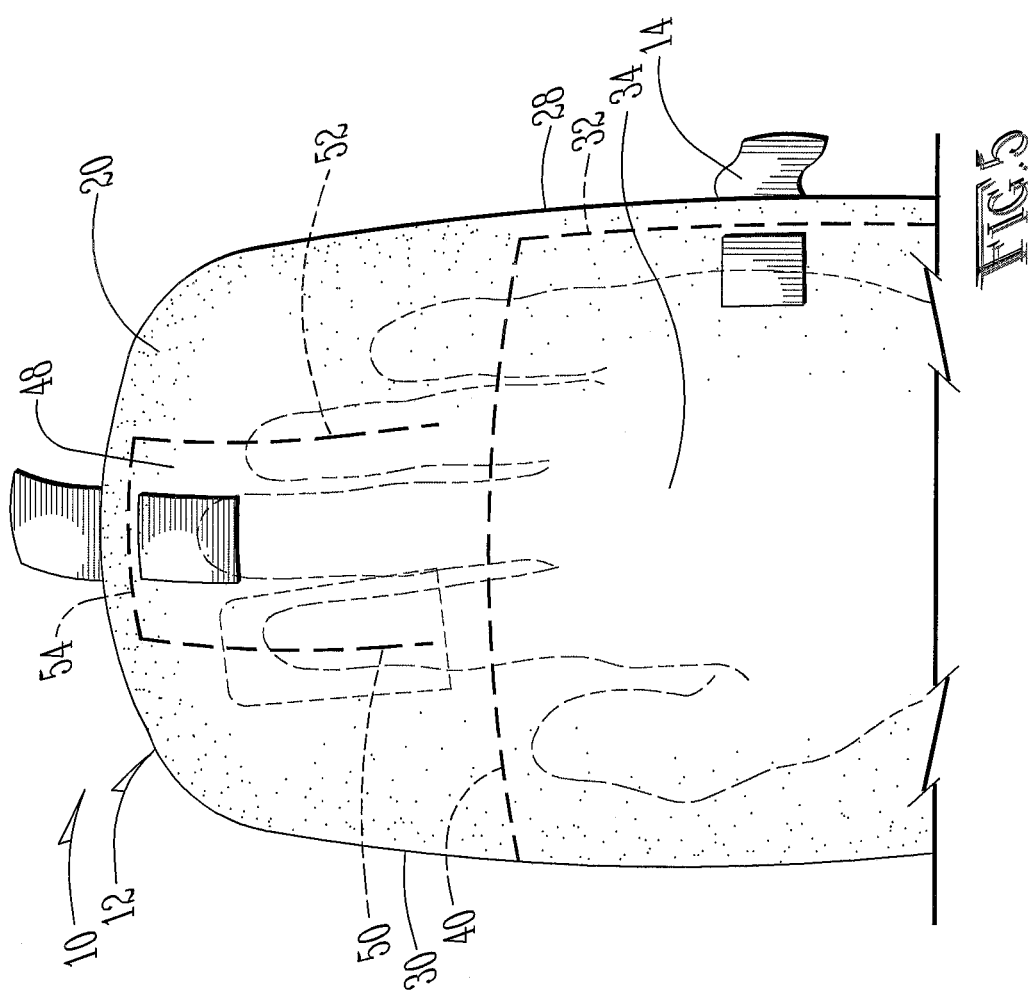
FIG. 5 is a top view of the second end of the second preferred embodiment of the medical hand and arm protection apparatus.

The second end 20 of the protective shell 12 also has one or more perforations 46 which extend longitudinally along the second end 20. Through use of the perforations 46, the medical professional can check the medical equipment attached to the patient's fingers, such as a pulse oximeter. The perforations 46 allow the medical professional to break the perforation 46 and use their fingers to pull the foam on either side of the broken perforation apart to view the interior of the second end 20 of the protective shell 12. In an alternative preferred embodiment, as shown in FIG. 5, the second end 20 of protective shell 12 has one or more perforated panels 48 created by two longitudinally extending perforations 50, 52 intersected by one laterally extending perforation 54.

On the first side 28 of the protective shell 12 is one or more connecting straps 14. In the preferred embodiment, the connecting strap 14 is a VELCRO® connector where one piece of the VELCRO® connector is attached to the perforated panels 34, 36, 38 (releasable flaps 62, 64, 66 when the perforations are broken) of the shell 12 and a complementary piece of the VELCRO® connector is attached to the bottom section 26 of the shell 12, directly below perforated panels 34, 36, 38. With the connecting strap 14, the medical professional can check the patient's IV or other medical equipment connections by breaking the perforations of the perforated panels 34, 36, 38, thus forming releasable flaps 62, 64, 66. The releasable flap(s) can then be secured by the connecting strap(s) 14. The connecting strap 14 need not be a VELCRO® connector, but instead can be any other means for connection as known to those skilled in the art, including hook and loop fasteners. In the alternative preferred embodiment where there are perforated panels in the second end of the protective shell 12, connecting straps 14 may also be utilized.

Attached to the first side 28 of protective shell 12 is a sheet 16. The sheet 16 is attached to the protective shell 12 by means well-known to those skilled in the art, including but not limited to, gluing and stitching. The sheet 16 is preferably attached directly below perforated panel 36. The sheet 16 is preferably 16 inches in length and 16 inches in width, but it may vary in size. The sheet 16 is made of a durable, nonabrasive, nonflammable, impermeable material that is capable of withstanding tearing and puncturing, such as the material used for medical gowns. Once the patient's hand and arm is inserted into the surgical hand and arm protector 10, the sheet 16 is tucked underneath the patient. As a result, the body weight of the patient anchors the protector 10 to the patient's side. When both the patient's arms and hands are in hand and arm protectors 10, the two sheets 16 may be connected underneath the patient to further secure the arms to the side of the patient. The means for connecting the two sheets 16 is of the type that is well-known to those skilled in the art.

In a second preferred embodiment, as shown in FIG. 6, the protective shell 12 has a top section 24 and a bottom section 26. The top section 24 is the top cross-section of the shell 12, while the bottom section 26 is the bottom cross-section of the shell 12. Instead of having perforated panels 34, 36, 38 in top section 24 as in the first preferred embodiment, the top section 24 preferably has perforations 56, 58, 60. Perforations 56, 58, 60 extend laterally across the entire top section 24 of shell 12. Perforations 56, 58, 60 allow the medical professional to break the perforation and use their fingers to pull the foam on either side of the broken perforation apart to view the interior of the protective shell 12. Perforation 56 is in the hand region of the surgical arm protector 10. Perforation 58 is in the wrist region and perforation 60 is in the forearm and elbow region. While three laterally extending perforations is preferred, the number of perforations and their location can vary. In both the first and second preferred embodiments, each component of the hand and arm protection apparatus is preferably biodegradable.

The present invention has been described with certain preferred and alternative embodiments that are intended to be exemplary only and not limiting to the full scope of the invention.

What is claimed is:

1. A medical hand and arm protection apparatus comprising:
   (a) a protective shell operable to receive a hand and an arm of a patient, wherein said protective shell has an open end and a closed end, wherein a middle section of said protective shell extends between said open end and said closed end, wherein a first perforation extends laterally around less than a perimeter of said middle section, wherein said first perforation is operable to be broken to access an interior of said protective shell; and
   (b) a sheet having a first end and a second end, wherein said first end is attached to said protective shell by a connector and said second end is not attached to said protective shell, wherein said second end of said sheet is operable to be tucked underneath said patient's body after said arm of said patient is received by said protective shell.

2. The medical hand and arm protection apparatus of claim 1, wherein a second perforation extends laterally around a circumference of said open end of said protective shell.

3. The medical hand and arm protection apparatus of claim 1, wherein a third perforation extends longitudinally at said closed end of said protective shell.

4. The medical hand and arm protection apparatus of claim 1, wherein said protective shell is made of foam.

5. The medical hand and arm protection apparatus of claim 1, wherein said sheet of said medical hand and arm protection apparatus is connectable to a sheet of a second medical hand and arm protection apparatus.

6. The medical hand and arm protection apparatus of claim 1, wherein said connector is glue.

7. The medical hand and arm protection apparatus of claim 1, wherein said connector is stitching.

* * * * *